United States Patent [19]

Schlosser et al.

[11] 4,047,037

[45] Sept. 6, 1977

[54] GAMMA RAY CAMERA FOR NUCLEAR MEDICINE

[75] Inventors: Philip A. Schlosser; John W. Steidley, both of Columbus, Ohio

[73] Assignee: The Ohio State University, Columbus, Ohio

[21] Appl. No.: 656,304

[22] Filed: Feb. 9, 1976

[51] Int. Cl.$^2$ .............................................. G01T 1/22
[52] U.S. Cl. .................................... 250/370; 250/505
[58] Field of Search ................ 250/370, 371, 363 S, 250/505

[56] References Cited

U.S. PATENT DOCUMENTS

| | | |
|---|---|---|
| 3,812,360 | 5/1974 | Tkyva .................................. 250/370 |
| 3,812,361 | 5/1974 | Prag et al. ........................... 250/370 |
| 3,936,639 | 2/1976 | Barrett ............................. 250/505 X |
| 3,943,366 | 3/1976 | Platz et al. .......................... 250/505 |
| 3,988,589 | 10/1976 | Leask ................................. 250/505 |

Primary Examiner—Davis L. Willis
Attorney, Agent, or Firm—Sidney W. Millard

[57] ABSTRACT

An improved gamma camera arrangement wherein the spatially defined acceptance of gamma radiation from a source distribution of clinical interest is enhanced by a unique collimator structure. Aliasing frequencies otherwise derived from an orthogonal strip detector array are identified and avoided through a structural geometry wherein collimator resolution is greater than or equal to about 1.7(l), where, l, is the strip spacing of the array.

21 Claims, 19 Drawing Figures

Fig.8(a) MTF

Fig.8(b) MTF

Fig.8(c) MTF

Fig.8(d) MTF

GAMMA RAY CAMERA FOR NUCLEAR MEDICINE

The invention described herein was made in the course of work under a grant or award from the Department of Health, Education and Welfare.

BACKGROUND

The field of nuclear medicine has long been concerned with techniques of diagnosis wherein radio pharmaceuticals are introduced into a patient and the resultant distribution or concentration thereof as evidenced by gamma ray intensities is observed or tracked by an appropriate system of detection. An important advantage of the diagnostic procedure is that it permits non-invasive investigation of a variety of conditions of medical interest. Approaches to this investigative technique have evolved from early pioneer procedures wherein a hand-held radiation counter was utilized to map body contained areas of radioactivity to more current systems for imaging gamma ray source distributions, in vivo. In initially introduced practical systems, scanning methods were provided for generating images, such techniques generally utilizing a scintillation-type gamma ray detector equipped with a focusing collimator which moved continuously in selected coordinate directions, as in a series of parallel sweeps, to scan regions of interest. A drawback to the scanning technique resides in the necessarily longer exposure times required for the derivation of an image. For instance, such time elements involved in image development generally are overly lengthy to carry out dynamic studies of organ function.

By comparison to the rectilinear scanner described above, the later developed "gamma camera" is a stationary arrangement wherein an entire region of interest is imaged at once. As initially introduced the stationary camera systems generally utilized a larger diameter sodium Iodide, Na I (Tl) crystal as a detector in combination with a matrix of photomultiplier tubes. For additional information concerning such camera, see:

I. Anger, H. O., "A New Instrument For Mapping Gamma Ray Emitters," *Biology and Medicine Quarterly Report* UCRL-3653, 1957.

A multiple channel collimator is interposed intermediate the source containing subject of investigation and the scintillation detector crystal. When a gamma ray emanating from the region of investigative interest interacts with the crystal, a scintillation is produced at the point of gamma ray absorption and appropriate ones of the photomultiplier tubes of the matrix respond to the thus generated light to develop output signals. The original position of gamma ray emanation is determined by position responsive networks associated with the outputs of the matrix.

A continually sought goal in the performance of gamma cameras is that of achieving a high resolution quality in any resultant image. Particularly, it is desirable to achieve this resolution in combination with concomitant utilization of a highly versatile radionuclide or radiolabel, 99m-Technetium, having a gamma ray or photon energy in the region of 140 keV.

The resolution capabilities of gamma cameras incorporating scintillation detector crystals, inter alia, is limited both by the light coupling intermediate the detector and phototube matrix or array as well as by scatter phenomena of the gamma radiation witnessed emanating from within the in vivo region of investigation. Concerning the latter scattering phenomena, a degradation of resolution occurs from scattered photons which are recorded in the image of interest. Such photons may derive from Compton scattering into trajectories wherein they are caused to pass through the camera collimator and interact photoelectrically with the crystal detector at positions other than their point of in vivo derivation. Should such photon energy loss to the Compton interaction be less than the energy resolution of the system, it will effect an off-axis recordation in the image of the system as a photopeak photon representing false spatial information or noise. As such scattered photons record photopeak events, the noise increase and consequent resolution quality of the camera diminishes. For the noted desirable 140 keV photons, the scintillation detector-type camera energy resolution is approximately 22 keV. With this resolution, photons which scatter through an angle from 0° to about 70° will be seen by the system as such photopeak events.

A continuing interest in improving the resolution qualities of gamma cameras has lead to somewhat extensive investigation into imaging systems incorporating relatively large area semiconductor detectors. Such interest has been generated principally in view of theoretical indications of an order of magnitude improvement in statistically limited resolution to provide significant improvements in image quality. In this regard, for example, reference may be made to the following publications:

II. R. N. Beck, L. T. Zimmer, D. B. Charleston, P. B. Hoffer, and N. Lembares, "The Theoretical Advantages of Eliminating Scatter in Imaging Systems," *Semiconductor Detectors in Nuclear Medicine*, (P. B. Hoffer, R. N. Beck, and A. Gottschalk, editors), Society of Nuclear Medicine, New York, 1971, pp. 92–113.

III. R. N. Beck, M. W. Schuh, T. D. Cohen, and N. Lembares, "Effects of Scattered Radiation on Scintillation Detector Response, "*Medical Radioisotope Scintigraphy*, IAEA, Vienna, 1969, Vol. 1, pp. 595–616.

IV. A. B. Brill, J. A. Patton, and R. J. Baglan, "An Experimental Comparison of Scintillation and Semiconductor Detectors for Isotope Imaging and Counting," *IEEE Trans. Nuc. Sci.*, Vol. NS-19, No. 3, pp. 179–190, 1972.

V. M. M. Dresser, G. F. Knoll, "Results of Scattering in Radioisotope Imaging," *IEEE Trans. Nuc. Sci.*, Vol. NS-20, No. 1, pp. 266–270, 1973.

Particular interest on the part of investigators has been paid to detectors formed as hybridized diode structures fashioned basically of germanium. To provide discrete regions for spatial resolution if impinging radiation, the opposed parallel surfaces of the detector diodes may be grooved or similarly configured to define transversely disposed rows and columns, thereby providing identifiable discrete regions of radiation response. Concerning such approaches to treating the detectors, mention may be made of the following publications:

VI. J. Detko, "Semiconductor Dioxide Matrix for Isotope Localization, "*Phys. Med. Biol.*, Vol. 14, No. 2, pp. 245–253, 1969.

VII. J. F. Detko, "A Prototype, Ultra Pure Germanium Orthogonal Strip Gamma Camera," *Proceedings of the IAEA Symposium on Radioisotope Scintigraphy*, IAEA/SM-164/135, Monte Carlo, October 1972.

VIII. R. P. Parker, E. M. Gunnerson, J. L. Wankling, and R. Ellis, "A Semiconductor Gamma Camera with Quantitative Output," *Medical Radioisotope Scintigraphy.*

IX. V. R. McCready, R. P. Parker, E. M. Gunnerson, R. Ellis, E. Moss, W. G. Gore, and J. Bell, "Clinical Tests on a Prototype Semiconductor Gamma-Camera," *British Journal of Radiology*, Vol. 44, 58–62, 1971.

X. Parker, R. P., E. M. Gunnerson, J. S. Wankling, R. Ellis, "A Semiconductor Gamma Camera with Quantitative Output," *Medical Radioisotope Scintigraphy*, Vol. 1, Vienna, IAEA, 1969, p. 71.

XI. Detko, J. F., "A Prototype, Ultra-Pure Germanium, orthogonal-Strip Gamma Camera," *Medical Radioisotope Scintigraphy*, Vol. 1, Vienna, IAEA, 1973, p. 241.

XII. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in *IEEE Trans. Nucl. Sci.*, Vol. NS-21, No. 1 February 1974, p. 658.

XIII. Owen, R. B., M. L. Awcock, "One and Two Dimensional Position Sensing Semiconductor Detectors," *IEEE Trans. Nucl. Sci.*, Vol. NS-15, June 1968, p. 290.

In the more recent past, investigators have shown particular interest in forming orthogonal strip matrix detectors from p-i-n semiconductors fashioned from an ultra pure germanium material. In this regard, reference is made to U.S. Pat. No. 3,761,711 as well as to the following publications:

XIV. J. F. Detko, "A Prototype, Ultra Pure Germanium, Orthogonal Strip Gamma Camera," *Proceedings of the IAEA Symposium on Radioisotope Scintigraphy*, IAEA/SM-164/135, Monte Carlo, October, 1972.

XV. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in *IEEE Trans. Nucl. Sci.*, Vol. NS-21, No. 1, February 1974, p. 658.

High purity germanium detectors promise numerous advantages both in gamma camera resolution as well as in economic feasibility or practicality. For instance, by utilizing high purity germanium as a detector, lithium drifting arrangements and the like for reducing impurity concentrations are avoided and the detector need only be cooled to requisite low temperatures during its clinical operation. Readout from the orthogonal strip germanium detectors is described as being carried out utilizing a number of techniques, for instance, each strip of the detector may be connected to a preamplifier-amplifier channel and thence directed to an appropriate logic function and visual readout. In another arrangement, a delay line readout system is suggested with the intent of reducing the number of preamplifiers-amplifier channels, and a technique of particular interest utilizes a charge aplitting method. With this method or technique, position sensitivity is obtained by connecting each contact strip of the detector to a charge dividing resistor network. Each end of each network is connected to a virtual earth, charge sensitive preamplifier. When a gamma ray interacts with the detector, the charge released enters the string of resistors and divides in proportion to the amount of resistance between its entry point in the string and the preamplifiers. Utilizing fewer preamplifiers, the cost and complexity of such systems is advantageously reduced. A more detailed description of this readout arrangement is provided in:

XVI. Gerber, M. S., Miller, D. W., Gillespie, B., and Chemistruck, R. S., "Instrumentation For a High Purity Germanium Position Sensing Gamma Ray Detector," *IEEE Trans. on Nucl. Sci., Vol. NS-22*, No. 1, February, 1975, p. 416.

To achieve requisite performance and camera image resolution, it is necessary that substantially all sources of noise or false information within the system be accounted for. In the absence of adequate noise resolution, the performance of the imaging systems may be compromised to the point of impracticality. Until the more recent past, charge-splitting germanium detector arrangements have not been considered to be useful in gamma camera applications in consequence of thermal noise anticipated in the above-noted resistor divider networks, see publication VII, supra. However, as will be evidenced in the description to follow, such considerations now are moot.

Another aspect in the optimization of resolution of the images of gamma cameras resides in the necessarily inverse relationship between resolution and sensitivity. A variety of investigations have been conducted concerning this aspect of camera design, it being opined that photon noise limitations, i.e. statistical fluctuations in the image, set a lower limit to spatial resolution. Further, it has been pointed out that the decrease in sensitivity witnessed in conventional high resolution collimators may cancel out any improvements sought to be gained in image resolution. A more detailed discourse concerning these aspects of design are provided, for instance, in the following publications:

XVII. E. L. Keller and J. W. Coltman, "Modulation Transfer and Scintillation Limitations in Gamma Ray Imaging," *J. Nucl. Med.* 9, 10, 537–545 (1968).

XVIII. B. Westerman, R. R. Sharma, and J. F. Fowler, "Relative Importance of Resolution and Sensitivity in Tumor Detection," *J. Nucl. Med.* 9, 12, 638–640 (1968).

More recent investigation of gamma camera performance has identified still another operational phenomenon tending to derogate from spatial resolution quality. This phenomenon is referred to as "aliasing" and represents a natural outgrowth of the geometry of the earlier noted orthogonal strip germanium detector. The phenomenon further represents a subject to which the instant invention will be seen, inter alia, to be considered in detail. A more detailed discussion of the phenomena is provided at:

XIX. J. W. Steidley, et al., "The Spatial Frequency Response of Orthogonal Strip Detectors," IEEE Trans. Nuc. Sci., February, 1976.

SUMMARY

The present invention is addressed to an improved gamma camera arrangement wherein the spatially defined acceptance of radiation emanating from a regionally disposed source is enhanced to achieve significant improvement in imaging resolution. The invention recognizes a highly important operational aspect of gamma cameras utilizing orthogonal strip germanium detectors as residing in the geometrically inherent creation of spurious spatial frequencies. These frequencies, termed "aliasing frequencies" have been determined to result from the sampling performance of the noted orthogonal strip type detector and their influence upon such camera systems ultimately may be found to dictate the resolution capacities of imaging systems utilizing the noted detector arrangement.

An important aspect and object of the invention is to provide, in a gamma camera incorporating an orthogonal strip array semiconductor detector for deriving spatial and energy level information corresponding with a source distribution, an improved collimator arrangement serving to limit the frequency content of the source reaching the detector to frequencies less than about one half of the sampling frequency in one dimension of the strip array or matrix of the detector.

As another aspect and object of the invention, an improved collimator arrangement is provided for a gamma camera of the type described having an orthogonal strip array semiconductor detector wherein the collimator arrangement is present as an array of adjacently disposed channels having sides defining a square cross-section and aligned normally to the receiving surface of the detector. The array of channels is configured to define a septal thickness, T, intermediate the channels. Further, the effective thickness of the collimator, represented as $A_E$, exhibited wherein $A_E = A - 2/\mu(E)$, where $\mu(E)$ is the attenuation coefficient of the surface material of the channels of the collimator for a given energy level E of a radiation source. The collimator is formed to provide a collimator resolution, $R_c$, equal to or greater than about 1.7 (l) and is configured in substantial satisfaction of the expression:

$$R_c = (D/A_E)(A + B + C)$$

where C is the distance from the inwardly disposed plane defining side of the collimator to the midplane of the orthogonal strip detector; A is the thickness of the collimator and B is the distance between the source of radiation and the outwardly disposed plane defining side of the collimator; D is the effective diameter of the noted channels; and l is the strip spacing of the orthogonal strip array detector.

The invention further contemplates as an object, the improved gamma arrangement described above wherein the septal wall thickness, T, of the noted collimator is equal to or about:

$$\frac{-2D\ln P}{\mu(E)A + \ln P}$$

wherein, P, is the penetration fraction of the side defining material of the collimator, this fraction having a value about equal to or less than 0.05.

As another feature in object of the invention, a collimator arrangement for a gamma camera system is provided, which in addition to exhibiting the advantageous operational characteristics described above, is fabricable utilizing sheet tungsten or tantalum or side channel material in consequence of a geometric configuration rendering its manufacture practical. In this regard, the array of channels making up the collimator arrangement comprises a plurality of sheet members each being configured having a plurality of mutually equally spaced parallel slots of length equal to or about the height of the sheets and the concomitant collimator thickness. The slots are formed having a width corresponding with the thickness of the sheets themselves. The sheet members, once so configured, are assembled by being mutually internested to define the collimator array. Preferably, the slots are formed within the sheet member by chemical milling techniques to achieve requisite tolerances for effecting control over streaming phenomena otherwise encountered in the performance of the camera system. Through the use of tungsten or tantalum components the septum thickness of the collimator array may be advantageously reduced for improved system efficiency, particularly for desired radiation energy levels, for instance, in the range of about 140 keV. The noted streaming phenomena may be contained within acceptable levels by maintaining the noted slot tolerances equal to or less than about 0.001 inch.

The invention further contemplates, as an object, the gamma camera arrangement and system as set forth hereinabove wherein, for a collimator resolution as above defined, the multichannel collimator array is configured having an optimized collimator geometric efficiency, $\phi_s$, where:

$$\theta_s = \left[\frac{0.282 D^2}{A_L(D + T)}\right]^2$$

for a channel cross-section of square configuration.

As another object, the invention contemplates a collimator arrangement for a gamma camera assembly of a variety operative to derive image defining information of the source distribution of gamma rays, such camera incorporating an orthogonal strip array semiconductor detector, the strips of which have a spatial frequency, 1/c, and center-to-center strip spacing, l. This collimator perferably is formed of a plurality of sheet members of height, h, each of the members being configured having a select number of parallel slots extending from one edge thereof along the dimension of the height. The slots extend a distance substantially equivalent to one half the height, h, and are mutually spaced in a regularly recurring manner to define a slot-to-slot pitch substantially equivalent to the side cross sectional dimension of one chamber within the collimator plus a predetermined tolerance dimension. Any two of the noted sheet members are joined by being mutually internested about select ones of the slots of each to form the parallel multiple channel collimator assembly.

Other objects of the invention will, in part, be obvious and will, in part, appear hereinafter.

The invention, accordingly, comprises the system and apparatus possessing the construction of elements and arrangement of parts which are exemplified in the following detailed disclosure.

For a fuller understanding of the nature and objects of the invention, reference should be had to the following detailed description taken in conjunction with the accompanying drawings.

BRIEF DESCRIPTION OF THE DRAWINGS

FIGS. 9a – d provide curves showing the results of aliasing correction as compared with the curves of FIGS. 8a –d, FIG. 9a looking to collimator design as an anti-aliasing filter;

DETAILED DESCRIPTION

As indicated in the foregoing discourse, during contemplated clinical utilization, a gamma camera arrangement according to the instant invention is used to image gamma radiation eminating from a region of radio pharmaceutical source distribution within a patient. Looking to FIG. 1, an exaggerated schematic representation of such a clinical environment is revealed generally at 10. The environment 10 schematically shows the cranial region 12 of a patient to whom has been administered a radiolabeled pharmaceutical, which pharmaceutical will have tended to concentrate within a region of investigative interest. Accordingly, radiation is depicted as emanating from this region 12 as the patient is positioned upon some supporting platform 14. Over the region 12 is positioned the head or housing 16 of a gamma camera. Housing 16 is pivotally supported at 18 from a beam 20. Beam 20, carrying a counter-weight 22, is pivotally supported at 24 in dual axis gimbal fashion from an upstanding support 26. Support 26 is fixedly attached to and extends from a base member 28. As is represented only in dotted line and generalized fashion, the head 16 is configured to retain an ultra-pure germanium orthogonal strip type semiconductor detector 30 as well as resistordivider networks tapping the detector and preamplification stages (not shown in FIG. 1) within a vacuum chamber 32. Chamber 32 is retained at a predetermined low temperature, for instance 77° K by an appropriate cryogenic system during operation of the head 16 to provide one aspect of necessary detector and electronic noise diminution. Adjacent to the detector 30 and disposed intermediate the detector and the patient-retained source of radiation 12, is a multi-channel collimator 33, the design and structure of which represents a highly important aspect of the instant invention.

Figure 1:
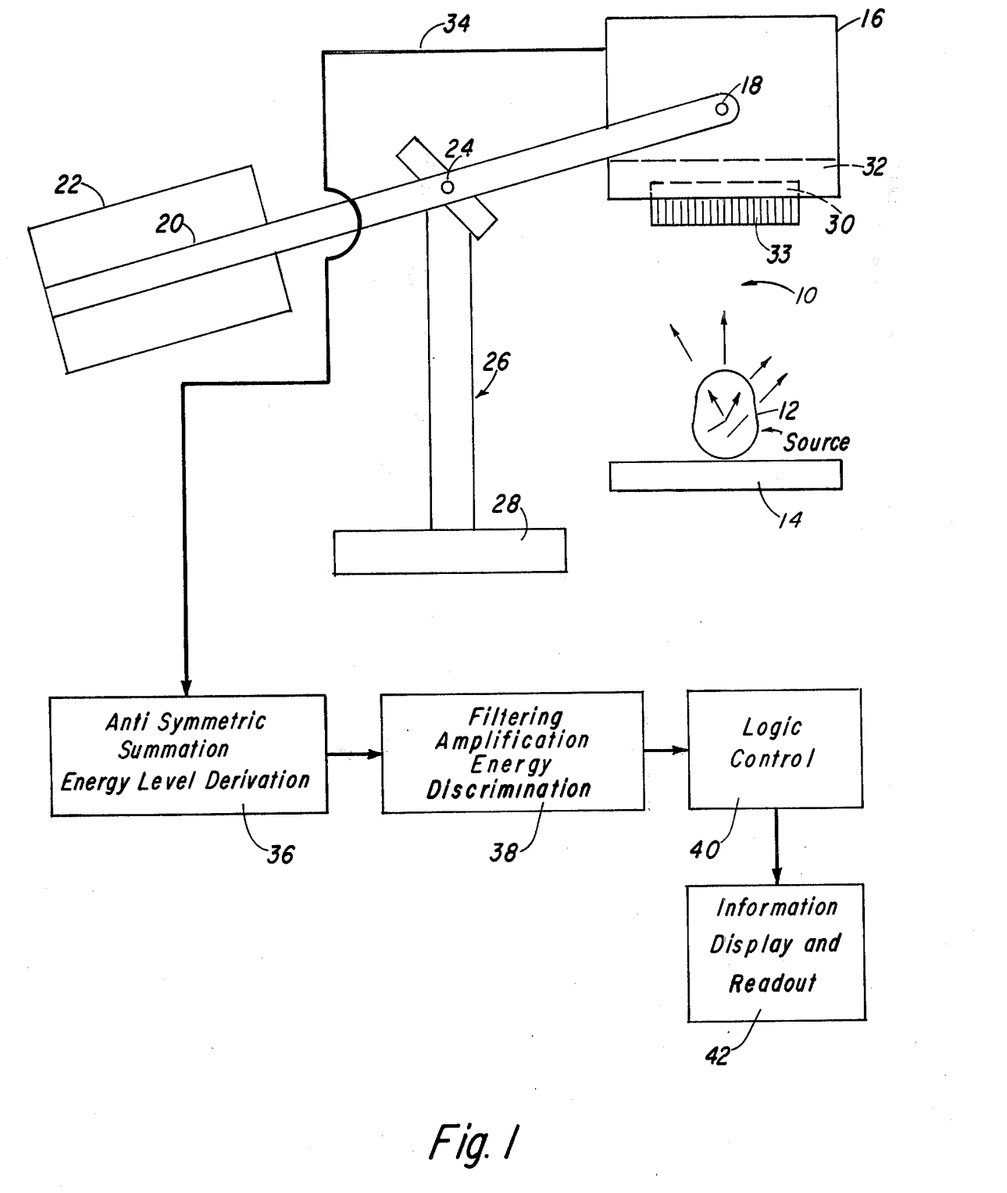
FIG. 1 is a schematic representation of a gamma camera arrangement as may utilize the improvements of the invention, showing, in block schematic form, control functions of the system.

During the operation of the gamma camera, radiation emanating from source 12 is spatially coded initially at collimator 33 by attenuating or rejecting off-axis radiation representing false image information. That radiation passing collimator 33 impinges upon detector 30 and a significant portion thereof is converted to discrete charges or image signals. Detector 30 is so configured as to distribute these signals to resistor chains as well as select preampliciation stages retained within chamber 32 to provide initial signals representative of image spatial information along conventional coordinate axes as well as representing values for radiation energy levels. This data then is introduced, as represented schematically by line 34, to filtering and logic circuitry which operates thereupon to derive an image of optimized resolution and veracity. In the latter regard, for instance, it is desired that only true image information be elicited from the organ being imaged. Ideally, such information should approach the theoretical imaging accuracy of the camera system as derived, for instance, from the geometry of the detector structure 30 and collimator arrangement 33 as well as the limitations of the electronic filtering and control of the system. Instrumentation for achieving the latter function is described, for instance, in detail and the following publication which is incorporated herein by reference:

XX. Gerber, M. S., Miller, D. W., Gillespie, B., and Chemistruck, R. S., "Instrumentation for a High Purity Germanium Position Sensing Gamma Ray Detector," IEEE Trans. on Nucl. Sci., Vol. NS-22, No. 1, February 1975, p. 416.

Image spatial and energy level signals from line 34 initially, are introduced into Anti-Symmetric Summation and Energy Level Derivation represented at block 36. As is described in more detail later herein, the summation carried out at block 36 operates upon the charges directed into the resistive chains or networks associated with the orthogonal logic structuring of detector 30 to derive discrete signals or charge values corresponding with image element location. Additionally, circuitry of the function of block 36 derives a corresponding signal representing the energy levels of the spatial information. The output of block 36 is directed to Filtering Amplification and Energy Discrimination functions as are represented at block 38. Controlled from a Logic Control function shown at block 40, function 38 operates upon the signal input thereto to accommodate the system to parallel and serially defined noise components through the use of Gaussian amplification or shaping, including trapezoidal pulse shaping of data representing the spatial location of image bits or signals. Similarly, the levels of incoming signals are evaluated, for instance, utilizing single channel analyzer components controlled by logic 40 to establish an energy level window for data received within the system. In this regard, signals falling above and below predetermined energy levels are considered false and are blocked. From Amplification and Discrimination stage 38 and Logic Control 40, the analyzed signals are directed into an Information Display and Readout Function, as is represented at block 42. Components within function block 42 will include display screens of various configurations, image recording devices, for instance, photographic apparatus of the instant developing variety, radiation readout devices and the like, which are controlled at the option of the system operator.

Figure 2:
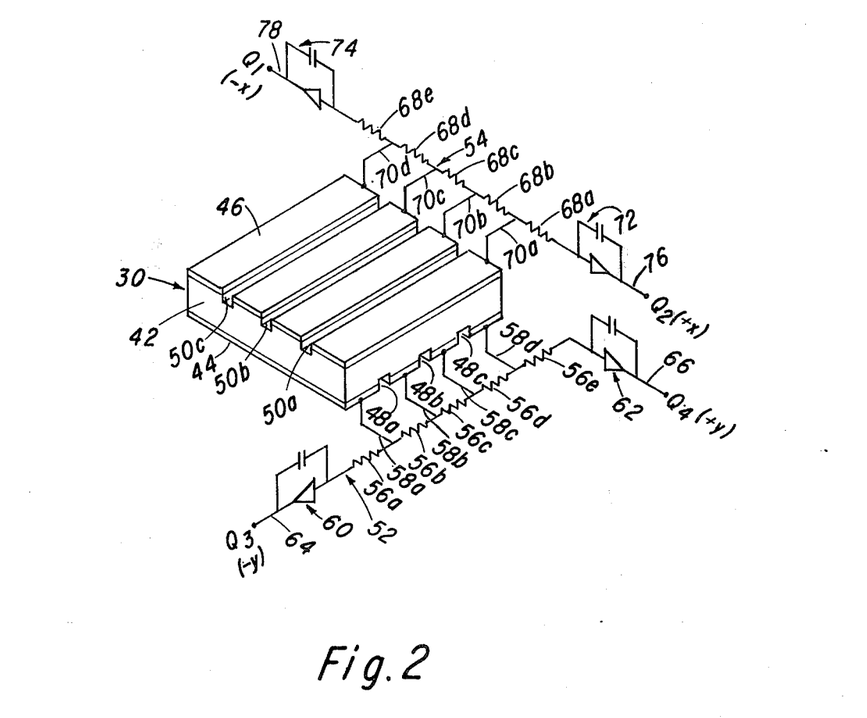
FIG. 2 is a pictorial representation of a solid state orthogonal strip high purity germanium detector incorporating a charge splitting resistor network in combination with preamplification electronics.

Looking to FIG. 2, an exaggerated pictorial representation of a portion of detector 30 is revealed. Detector 30 may be fabricated from p-type high purity germanium by depositing an n-type contact on one face and a p-type contact on the opposite face of a rectangular planar crystal. Accordingly, a high purity germanium region of the crystal, as at 42, serves as an intrinsic region between p-type sem-conductor region contacts 44 and n-type semiconductor region contacts as at 46. The intrinsic region 42 of the p-i-n detector forms a region which is depleted of electrons and holes when a reverse bias is applied to the contacts. Grooves as at 48a–48c are cut into the continuous p-type contact or region at one face of the detector to form strips of isolated p-type semiconductor material. On the opposite face of the detector, orthogonally disposed n-type semiconductor strips similarly are formed through the provision of grooves 50a–50c. Configured having this geometry, the detector 30 generally is referred to as an orthogonal strip detector or an orthogonal strip array semiconductor detector. The electrode strips about each of the opposed surfaces of detector 30, respectively, are connected to external charge splitting resistor networks revealed generally at 52 and 54. Resistor network 52 is formed of serially coupled resistors 56a–56e which, respectively, are tapped at their regions of mutual interconnection by leads identified, respectively, at 58a–58d extending, in turn, to the orthogonal strips. The opposed ends of network 52 terminate in preamplification stages 60 and 62, the respective outputs of which, at 64 and 66, provide spatial output data for insertion within the above described summation and energy level derivation function 36 to provide one orthogonal or coordinate output, for instance, designated as a y-axis signal.

In similar fashion, network 54 is comprised of a string of serially coupled resistors 68a–68e, the mutual interconnections of which are coupled with the electrode strips at surface 46, respectively, by leads 70a–70 d. Additionally, preamplification stages as at 72 and 74 provide outputs, respectively, at lines 76 and 78 carrying spatial data or signals representative of image information along an X axis or axis orthogonally disposed with respect to the output of network 52.

With the assertion of an appropriate bias over detector 30, an imaging photon absorbed therewithin engenders ionization which, in turn, creates electron-hole pairs. The charge thusly produced is collected on the orthogonally disposed electrode strips by the bias voltage and such charge flows to the corresponding node of the resistor networks 52 and 54. Further, this charge divides in proportion to the admittance of each path to the virtual ground input of the appropriate terminally disposed preamplification stage. Such charge sensitive preamplification stage integrates the collected charge to form a voltage pulse proportional to that charge value. Assigning charge value designations $Q_1$ and $Q_2$, respectively, for the outputs 78 and 76 of network 54 and $Q_3$ and $Q_4$, respectively, for the output line 64 and 66 of network 52, the above-noted Summation and Energy Level Derivation functions for spatial and energy data may be designated. In this regard, energy information is derived from the sum of the signals $Q_1$ and $Q_2$ or signals $Q_3$ and $Q_4$. This determines the total charge collected on one set of strips which is proportional to the energy of the photon detector interaction. Antisymmetrical summation is utilized to generate spatial information through subtractive logic. For example, the x-channel spatial signal is obtained by subtracting $Q_1$ from $Q_2$, an x-channel signal of zero volts corresponding to an interaction which occurred below the middle electrode strips. Similarly, the y-channel spatial signal is obtained by subtracting $Q_3$ from $Q_4$. The spatial channels of the imaging system use differential Gaussian-trapezoidal pulse shaping amplifiers, while the energy channel operating in conjunction with the Logic Control energy discrimination function described in connection with block 40, utilizes Gaussian pulse shaping and summing in carrying out requisite imaging control. As noted above, the operational environment of the detector 30 as well as the charge splitting resistor networks 52 and 54 and associated amplification stages is one within the cryogenic region of temperature for purposes of avoiding Johnson noise characteristics and the like.

As a prelude to a more detailed consideration of the spatial resolution of gamma radiation impinging upon the entrance components of the gamma camera, some value may be gleaned from an examination of more or less typical characteristics of that impinging radiation. For instance, looking to FIG. 3 a portion of a patient's body under investigation is portrayed schematically at 90. Within this region 90 is shown a radioactively tagged region of interest 92, from which region the decay of radiotracer releases photons which penetrate and emit from the patient's body. These photons are then spatially selected by the collimator 33 and individually detected at detector 30 for ultimate participation in the evolution of an image display. The exemplary paths of seven such photons are diagrammed in the figure, as at a–g, for purposes of illustrating functions which the camera system is called upon to carry out. In this regard, the function of collimator 33 is to accept those photons which are traveling nearly perpendicular to the detector, inasmuch as such emanating rays provide true spatial image information. These photons are revealed at ray traces a and b, showing direct entry through the collimator 33 and appropriate interaction coupled with energy exchange within detector 30. Photon path c is a misdirected one inasmuch as it does not travel perpendicularly to the detector. Consequently, for appropriate image resolution such path represents false information which should be attenuated, as schematically portrayed. Scattering phenomena within collimator 33 itself or the penetration of the walls thereof allows "non-collimated" photons, i.e. ray traces d and e, to reach the detector. Photon path trace f represents Compton scattering in the patient's body. Such scattering reduces the photon energy but may so redirect the path direction such that the acceptance geometry of the camera, including collimator 33, permits the photon to be accepted as image information. Inasmuch as the detector 30 and its related electronics, as discussed generally above, measure both the spatial location and energy of each photon admitted by the collimator, the imaging system still may reject such false information.

Figure 3:
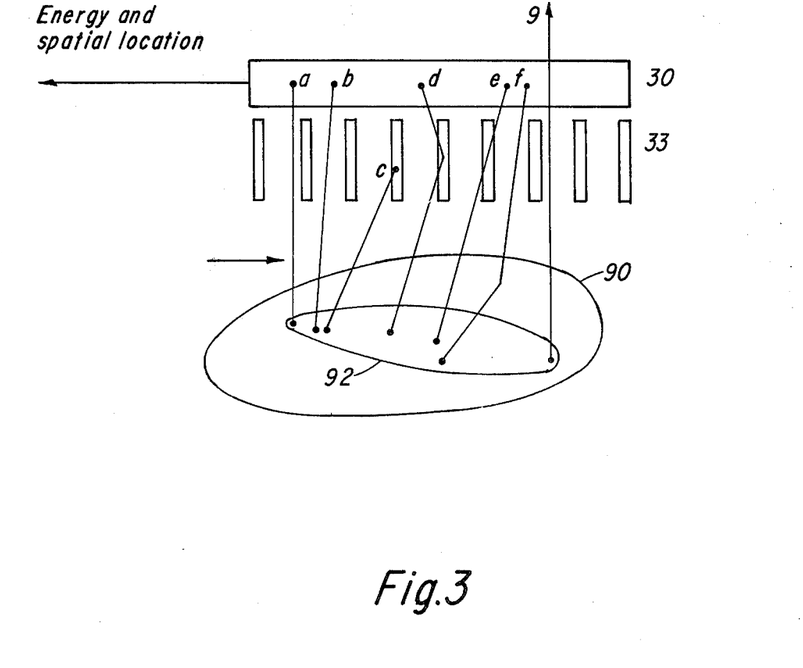
FIG. 3 is a schematic representation of a solid state orthogonal strip detector and a schematic collimator functionally associated therewith as such system components relate to a radiation source within a region of clinical interest.

For example, in the event of a Compton scattering of a photon either in the patient or collimator, the energy thereof may have been reduced sufficiently to be rejected by the energy discrimination window of the system. Photon path g represents a condition wherein detector 30 exhibits inefficient absorption characteristics such that the incident photon path, while representing true information, does not interact with detector 30. As in apparent from foregoing, each of the thousands of full energy photons which are abosrbed at detector 30 ultimately are displayed at their corresponding spatial location on an imaging device such as a cathode ray tube to form an image of the source distribution within region 92 of the patient. Of course, the clinical value of the gamma camera as a diagnostic implement is directly related to the quality of ultimate image resolution.

Figure 4A:
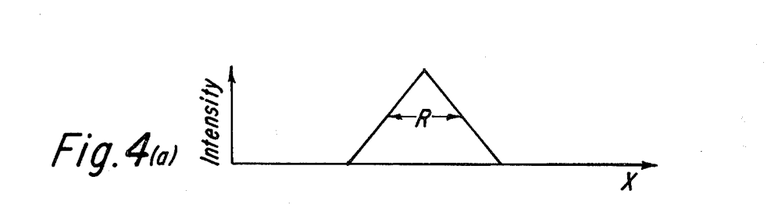
FIG. 4a – 4c are a schematic and graphical representation of the fundamental geometry associated with the interrelationship of a multi-channel collimator and a solid state detector as utilized in accordance with the present invention.
Figure 4B:
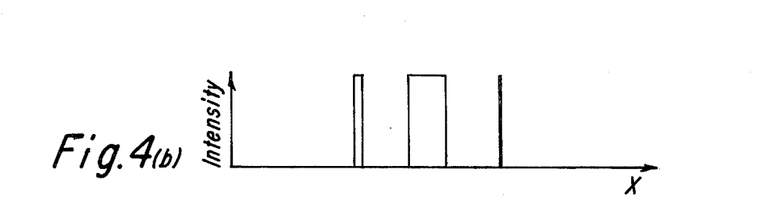
Figure 4C:
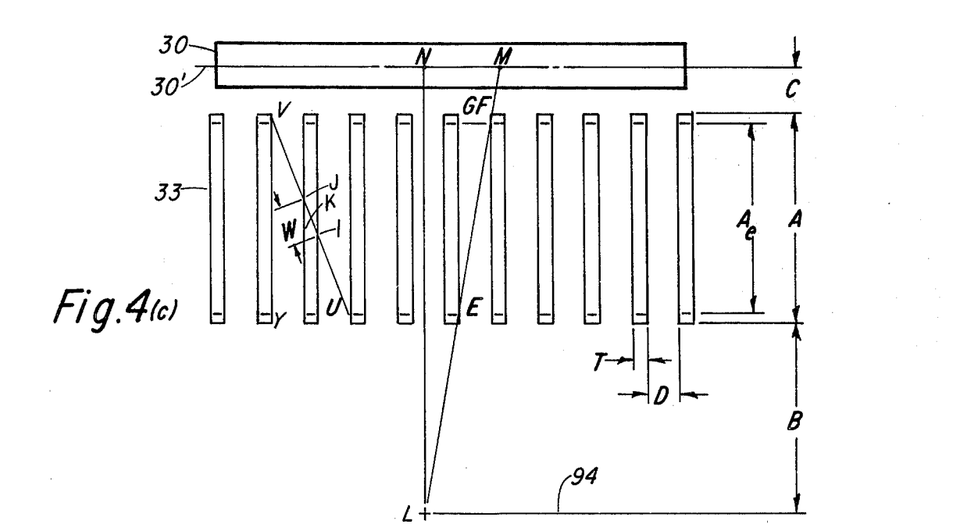

As is revealed from the foregoing discourse, the imaging resolution of the camera system is highly dependent upon the quality of collimation exhibited at the entrance of the camera by collimator 33. Generally, collimator 33 is of a multichannel, parallel-hole variety, its performance being dictated by its fundamental geometric dimensions, the material with which it is formed, and the technique of its fabrication. Referring to FIGS. 4a–4c, a designation of the geometric aspects of collimator 33, as such aspects relate to photon path travel, and spatial intensity distribution over the corresponding spatial axis of detector 30 are shown schematically. FIG. 4b shows the photon intensity distribution at the mid-plane 30' of detector 30 due to a line source of radiation at distance B from the collimator 33 outwardly disposed plane defining side. Note that the source position is designated "L". Source point L is located, for purposes of the instant analysis, within a plane 94 lying parallel to the outwardly disposed plane defining side of collimator 33 as well as its inwardly disposed plane defining side and the plane defined by the midpoint 30' of detector 30. The intensity distribution pattern of photons, revealed in FIG. 4b, is provided under the assumption that the collimator 33 is fixed in position. FIG. 4a, on the other hand, assumes that the collimator 33 moves during an exposure and produces, in consequence, a triangular intensity distribution pattern of photons. A location of value "R" designates a full width at half maximum (FWHM) spatial resolution. Such spatial or position resolution capability of the camera system may be defined utilizing several approaches. However, for the latter designation, FWHM, is derived from a consideration that if a very small spot of radiation exits at the object plane, the image generally will be a blurred spot with radially decreasing intensity. The position resolution then is defined as twice the radial distance at which the intensity is half of the center intensity.

Looking in particular to FIG. 4c, considering the similar triangles EFG and LMN, the resolution of collimator 33 generally may be expressed as:

$$R_c = (D/A_E)(A + B + C) \quad (1)$$

where
$A$ = the collimator thickness,
$A_E$ = the effective collimator thickness due to septial penetration,
$B$ = the source to collimator distance,
$C$ = the collimator to detector midplane distance and
$D$ = the effective diameter of each channel within the multi-channel collimator Effective diameter, D, is considered to be the square root of the cross-sectional area of a given collimator channel multiplied by 1.13.

The effective collimator thickness is given approximately by:

$$A_E = A - [2/\mu(E)] \quad (2)$$

where $\mu(E)$ is the attentuation coefficient of the collimator material at a photon energy, E.

For a given collimator material, sufficiently thick septal walls are required to reduce the number of photons or gamma rays that enter within a given collimator channel, penetrate the septal wall thereof and exit through an adjacent or other channel opening. Looking to FIG. 4c, one such gamma ray or photon path is traced as UV. Notes, that for this condition, the photon or ray passes through a collimator vane or channel side of thickness, T, along a minimum septal distance, W, thereby allowing the ray or photon to exit from a channel adjacent the channel of initial entrance. The fraction of photons or rays traveling UV that actually penetrate the septal wall is given by the penetration fraction:

$$P = \exp(-\mu(E) W). \quad (3)$$

It is considered the practice of the art to design the collimator structure such that the penetration fraction, P, is given a value less than about 5%. In this regard, mention may be made of the following publication:

XXI. H. O. Anger, "Radioisotope Cameras," *Instrumentation in Nuclear Medicine*, G. J. Hine, ed. Vol. 1, Academic Press, New York, 485-552 (1967).

The minimum septal distance, W, is found from the similar triangles IJK and UVY approximately as:

$$W = \frac{AT}{2D + T} \quad (4)$$

by assuming A is greater than $2D + T$ where T, as noted above, is the septal wall thickness. Solving equations (3) and (4) for the septal wall thickness, T, gives:

$$T = \frac{-2D\ln P}{\mu(E) A + \ln P} \quad (5)$$

The value, T, as set forth in equation (5) serves to define that minimal septal thickness for collimator 33 which is required for a given penetration fraction, P.

The geometric efficiency of the collimator is defined as the ratio of the number of gamma rays or photons which pass through the collimator to the number of photons or gamma arrays emitted by the source. Described in terms of the collimator parameters, such efficiency may be given by:

$$\theta_S = \left[\frac{KD^2}{A_E(D + T)}\right]^2 \quad (6)$$

where $K = 0.238$ for hexagonally packed circular holes and 0.282 for square holes or chambers in a square array.

As described above, the clinical value of the gamma camera imaging system stems principally from the systems capability for achieving quality image resolution.

Given the optimum image resolution which is practically available, it then is desirable to provide a design which achieves a highest efficiency for that resolution. For a collimator design, it is desirable to provide a low septal penetration fraction as well as a practical fabrication cost. Further, an inspection of equations (1) and (6) given above for collimator resolution and geometric efficiency, respectively, reveals that as resolution is enhanced, the efficiency of the collimator is diminished. In accordance with the instant invention, it has been determined that a multi-channel, parallel-hole collimator, the channels of which are configured having square cross sections represents a preferred geometric design freature. In this regard, where the latter are compared with collimator channels formed has round holes, hexagonally packed arrays or hexagonally packed bundles of tubes all of given identical dimensions, resolution remains equivalent, but the efficiency of the preferred square cross sectional channel array will be a factor of 1.4 times greater than the round hole design, while the efficiency of the hexagonally packed bundle of tubes will be intermediate the efficiency value of the above two designs. Consequently, as noted above, on the basis of maximum efficiency at a desired resolution, the square hole cross sectional chamber design is preferred.

Concerning the materials which may be selected for constructing the collimator, those evidencing a high density, high atomic number characteristic are appropriate for consideration. In particular, mention may be made of tungsten, tantalum and lead for the purpose at hand. The primary criterion for the material is that of providing a short mean free path at the photon energy level of interest. For the desirable energy level of 140 keV, the mean free path for photon attenuation is 0.012 inch in tungsten, 0.015 inch in tantalum and 0.016 inch in lead. Accordingly, for a selection based upon a mean free path for attenuation, tungsten represents the optimum collimator material. Heretofore, however, pragmatic considerations of machineability of workability have required a dismissal of the selection of tungsten and/or tantalum for collimator fabrication. For instance, for multichannel collimators having round channel cross sections, tungsten and tantalum are too difficult and, consequently, too expensive for drilling procedures and, in general hexagonally packed arrays providing such cross sections are restricted to fabrication in lead. Similarly, other designs formed out of the desired materials do not lend themselves to conventional machining and forming techniques, the cost for such fabrication being prohibitive even for the sophisticated camera equipment within which the collimator units are intended for utilization.

Figure 5:
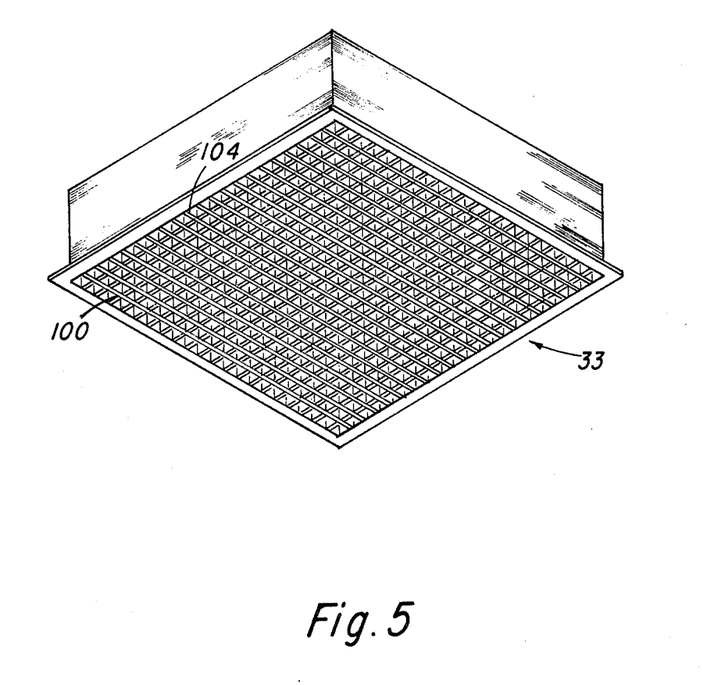
FIG. 5 is a pictorial representation of a collimator arry fabricated in accordance with a preferred embodiment of the instant invention.
Figure 6:
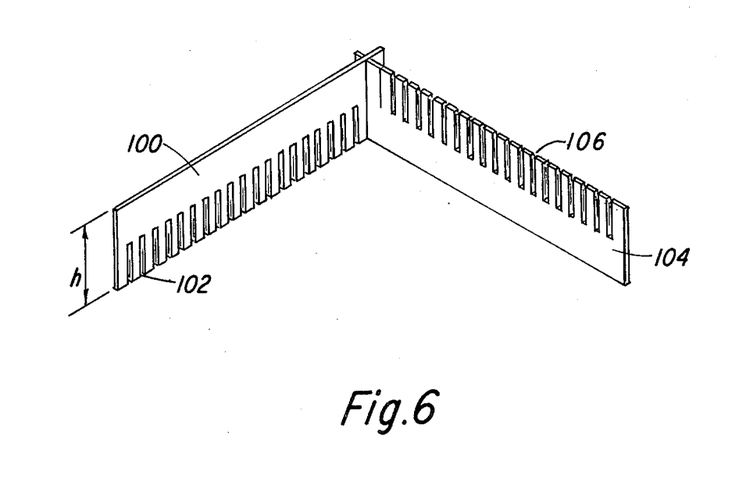
FIG. 6 is a pictorial view of two internested members of the collimator of FIG. 5.

In accordance with the instant invention, a square hole collimator design, fabricable utilizing the optimum material tungsten, is provided. Revealed in perspective fashion in FIG. 5, the collimator is shown to comprise an array of mutually parallel adjacently disposed channels having sides defining a square cross section. These channels extend to define inwardly and outwardly disposed sides which are mutually parallel and the channels are formed axially normally to each of these side planes. The highly desirable square structure shown in FIG. 5 is achieved utilizing the earlier described preferred tungsten material or tantalum, such materials normally being difficult or impractical to subject to more conventional manufacturing procedures. However, practical assembly of the collimator array 33 is achieved through the use of a plurality of discrete rectangularly shaped sheet members, as are revealed in the partial assembly of collimator 33 shown in FIG. 6. Referring to that figure, note that member 100 is formed as a flat rectangular sheet of height, $h$, corresponding with desired collimator thickness, A. Formed inwardly from one edge of member 100 are a plurality of slots spaced in regularly recurring parallel fashion and identified generally at 102. Slots 102 are formed having a height equivalent to $h/2$ and are mutually spaced to define a pitch or center-to-center spacing D plus T. The slots are formed having a width of $T + e$, where $e$ will be seen to be a tolerance. When the plurality of sheet members, for instance, as shown at 100 and 104 are vertically reversed in mutual orientation and the corresponding slots, respectively, as at 102 and 106 are mutually internested as shown, the collimator may be built-up to desired dimensions without recourse to elaborate forming procedures. Note that the width of slots 102 and 106 closely approximates the width of each of the sheet members within the array with a controlled allowance for tolerances. In determining the value for the above described pitch of the regularly recurring slots within the sheet members, assuming resolution criteria are met, a spacing may be selected to match the center-to-center electrode strip spacing of detector 30 or a multiple thereof so that the septal walls of the collimator 33 can be aligned with the less active grooves formed within the detector. Practical fabrication techniques are available for forming the slots as exemplified at 102 and 106. In particular, chemical milling or chemical machining techniques are avilable for this purpose. With such techniques, a wax type mask is deposited over the sheets to be milled, those material portions designated for removal being unmasked. The sheets then are subjected to selected etchants whereupon the slots are formed. Following appropriate cleaning, the sheet members then are ready for the relatively simple assembly build-up of a completed collimator. Through the use of such chemical milling techniques, desired tolerances in forming the slots are realizable. By utilizing the collimator structure shown in combination with optimal tungsten sheet material, a computable 35 to 40 percent improvement in collimator efficiency may be gained over round hole, hexagonally packed lead collimators of identical dimension, as well as a 50 to 80 percent improvement is spetal penetration characteristics and an average 5% improvement in geometric resolution. The collimator fabrication technique and structure are seen to offer several advantages over more conventional collimators structures. As evidenced from the foregoing, such advantages include the availability to the design of the superior shielding capabilities of tungsten; a simplicity of component design and consequent ease of assembly and the use of optimal square hole chamber geometry for maximum geometrical efficiency. However, to achieve optimal performance, the assembly technique necessarily introduces small gaps at the intersections of the septal walls of a completed collimator structure. These gaps exist by virtue of the tolerances required for the interlocking fit of the septal wall and the effect of gamma ray streaming through such gaps should be considered.

In earlier commentary herein, it has been noted that a septal penetration of five percent or less of impinging gamma radiation is preferred for collimator design. It follows, therefore, that the streaming factor for the particular collimator structure at hand should be assigned the same configurational parameter in the interest of desired unity of system design. Through utilization of a geometric analysis of a worst case condition, requisite lowest tolerance required for the interlocking fit of the septal walls and for a desired source to a collimator distance can be derived. Such analysis will reveal that the slot tolerance should preferably be no more than 0.001 inch and, more preferably, should be less than that to the extent of practical milling application.

In the discourse given heretofore concerning the functional inter-relationships of collimator 33 and detector 30, no commentary was provided concerning the effect of the discrete electrode strips of the detector upon ultimate image resolution. It has ben determined that, by virtue of their geometric configuration, orthogonal strip detectors, without appropriate correction, will introduce "alias" frequency components into the output of the system. For instance, in a purely linear system, the output of the camera would consist of the same spatial frequency components as the input except with the possibility of reduced contrast. Looking to FIGS. 7a–c, the aliasing phenomenon is demonstrated in connection with an exemplary and schematic representation of a strip electrode detector 130. In this worst case representation, no collimator is present and the electronic resolution is less than one strip width. Looking to FIG. 7a, a source distribution is shown as may be obtained, for instance, utilizing three discrete collimated point sources spaced at equal distances of 1.5 times the strip spacing. The reciprocal of the periodic spacing of the components depicted may be represented as, $v$. The source distribution shown is one with primary frequency components of $v_1 = 0$ and $v_2 = 2v_s/3$. Such source input is provided in the instant representation inasmuch as it combines the three qualities which accentuate an aliasing phenomenon, namely, a periodic input, 100% contrast, and a high signal-to-noise ratio.

Figure 7A:
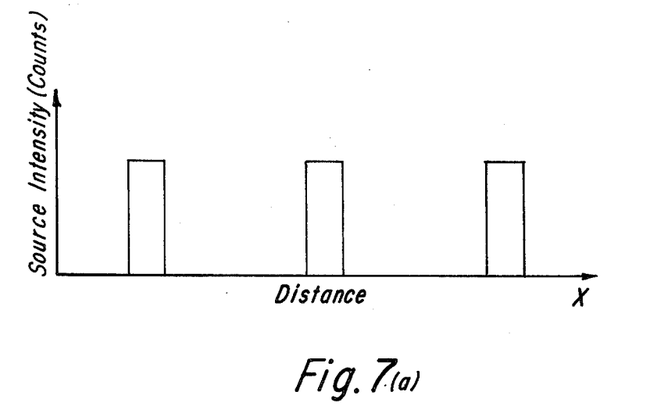
FIGS. 7a – c respectively and schematically depict representations of a source distribution as related with the geometry of an orthogonal strip detector and image readouts for illustrating aliasing phenomena.
Figure 7B:
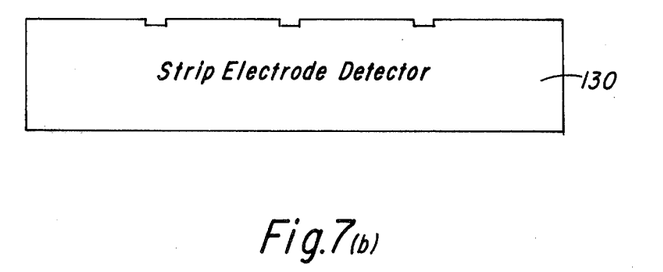
Figure 7C:
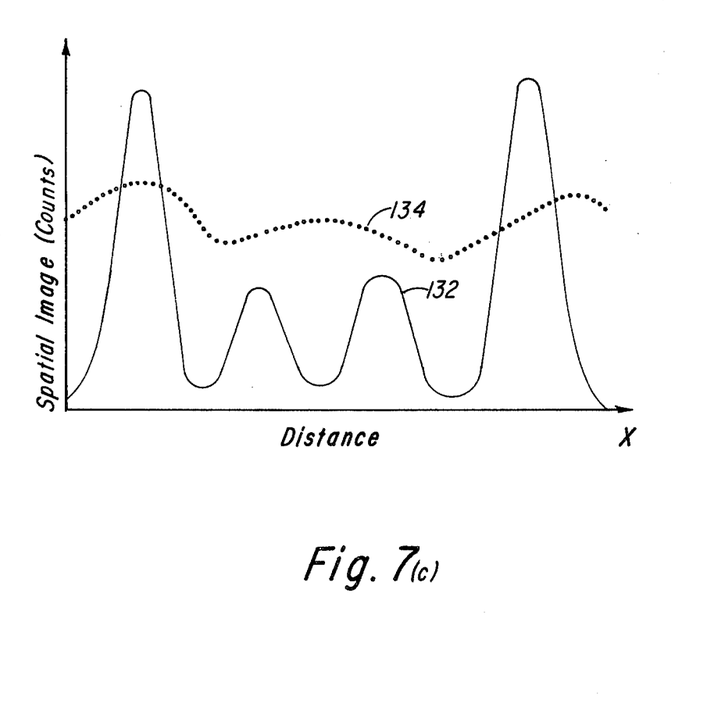

FIG. 7b reveals a portion of a strip electrode detector 130 having the earlier descibed detector region grooves aligned with respect to the input signals depicted at FIG. 7a. The one-dimensional spatial image which may be derived, for instance, from a multi-channel analyzer is shown in FIG. 7c as curve 132. By comparison, the corresponding spatial image which would be received within a system incorporating a collimator capable of resolving the input signals, a detector with strip spacing satisfying the anti-aliasing criterion and an anti-aliasing electronic channel, is revealed at 134. This image shows no aliased components.

Looking more particularly to the aliasing phenomenon represented at curve 132, the four lowest spatial frequency components revealed are:

1. a component at $v = 0$, a zero frequency component which represents the average value of the four peaks;
2. a component at $v = 2v_s/3$, which is the frequency equal to the reciprocal of the spacing betwen one of the two outer peaks and the average position of the two inner peaks;
3. a component at $v = v_s$, which is the frequency equal to the reciprocal of the spacing between each of the four peaks; and
4. a component at $v = v_s/3$, which is the frequency equal to the reciprocal of the spacing between the two outer peaks.

The first two components above are the fundamental source components, while the second two components are aliased components of the fundamental source components centered at the first harmonic of the strip sampling frequency.

Figure 8A:
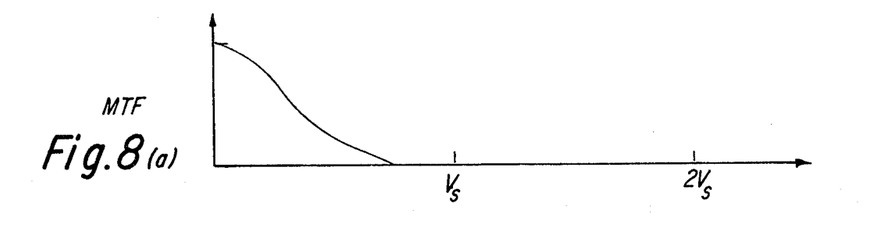
FIGS. 8a – d portray vertically aligned graphs relating modulation transfer function with respect to resolution as such data relates to aliasing phenomena, FIG. 8a showing collimator modulation transfer function ($MTF_c$) with FWHM resolution of 1.33 l, FIG. 8b showing a consequent alias frequency spectrum which is processed by the electronics of the camera system, FIG. 8c showing electronic MTF for given resolutions, and FIG. 8d showing camera system MTF's revealing aliasing introduced by the orthogonal strip solid state detector.
Figure 8B:
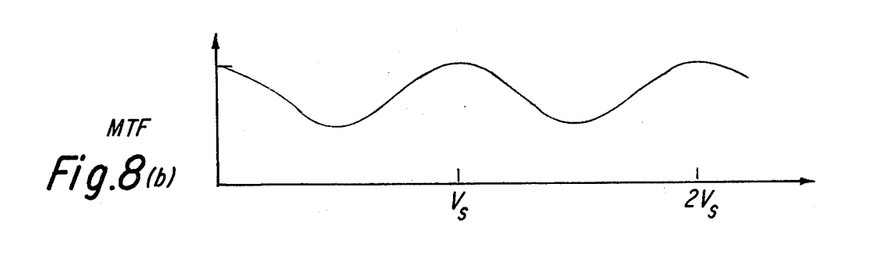
Figure 8C:
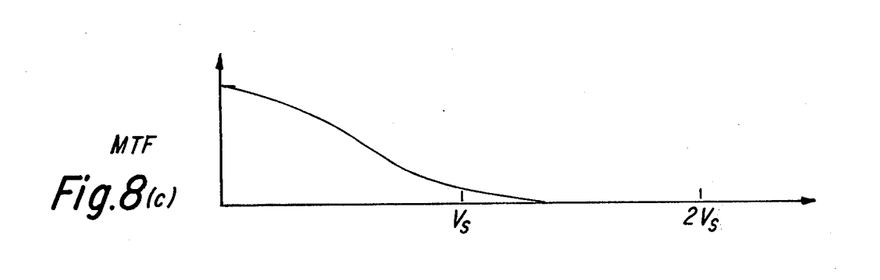
Figure 8D:
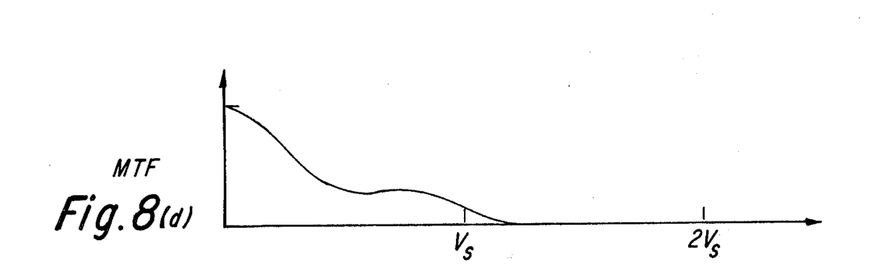

As a preclude to considering a typical representation of the spatial frequency response of a one-dimensional gamma camera as revealed in FIGS. 8a–d the modulation transfer functions (MTF) merit comment. As described in detail in publication (III) hereinabove, the MTF is a measure of spatial resolution that can be defined for linear systems and which takes into account the shape of an entire line spread function. The rationale for such description of spatial response arises from the fact that any object and its image can be described in terms of the amplitudes and phases of their respective spatial frequency components. The MTF is a measure of the efficiency with which modulation or contrast at each frequency is transferred by the imaging system from the object to the image. This is analogous to the temporal frequency response of an electronic amplifier or filter. Looking now to FIGS. 8a–8d MTF is plotted against spatial frequency, $v$, for a series of stages within a gamma camera not accommodating for aliasing phenomena. In FIG. 8a a collimator modulation transfer function ($MTF_c$) with FWHM resolution of 1.33 l is revealed, i.e., the curve distribution, incorporating some high frequency components, is representative of the signal passed to the semiconductor detector of the camera. FIG. 8b reveals the output frequency spectrum of the detector which is seen by the spatial channel electronics of the camera system. An aliased frequency spectrum is revealed, the input signal frequency spectrum being present in the output, centered at zero frequency and additional side bands of the primary input component are present, centered at integer multiples of the strip spacing or sampling frequency, $v_s = 1/l$. FIG. 8c represents the MTF of the electronics of the system, i.e., the transfer function of the spatial channel electronics, while FIG. 8d shows the product of the MTF values of the curves of FIGS. 8b and 8c. Accordingly, the curve of FIG. 8d shows the spatial frequency response of the entire system, including the introduction of spurious spatial frequency content in the system MTF, represented in the figure as the bump in the frequency range slightly below vs.

Figure 9A:
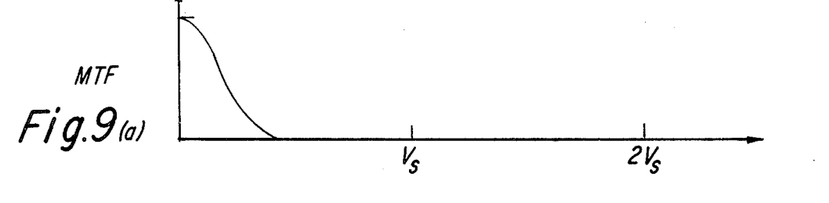
Figure 9B:
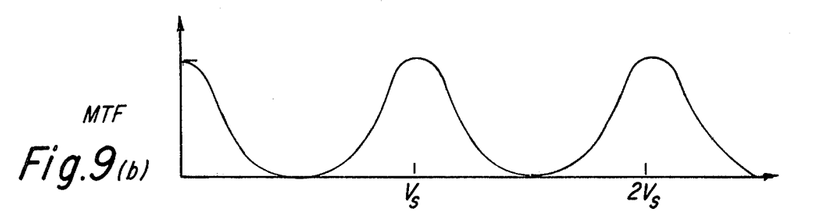
FIG. 9b showing a consequent aliasing frequency spectrum which is processed by the electronics of the system, FIG. 9c showing the consequences of electronics used for anti-aliasing post-filtering, and FIG. 9d showing total system MTF revealing the elimination of aliasing phenomena.
Figure 9C:
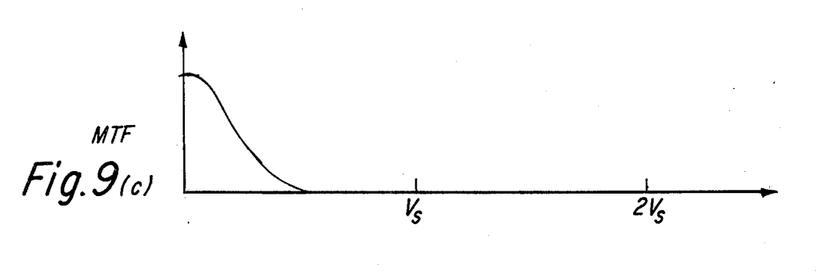
Figure 9D:
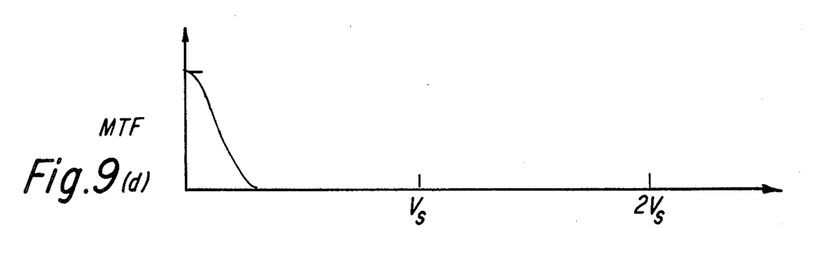

Looking by comparison now to FIGS. 9a–d the effect of inserted correction on the part of the collimator design and structure of the instant invention is revealed. In accordance with the invention, the collimator 33 design is selected to provide an MTF prefilter to limit the spatial frequency content seen by the detector 30 to frequencies less than $v_s/2$. Accordingly, FIG. 9a reveals that the collimator MTF is forced to a zero value at spectrum position $v_s/2$. Such design insures that the fundamental input frequency components and the first harmonic frequency components centered at $v_s$ do not overlap and this condition obtains in FIG. 9b, that Figure revealing the alias frequency spectrum which is processed by the electronic pickoff arrangement of the camera from the detector. The spatial channel electronics complete the anti-aliasing filter system by insuring that no spatial frequencies greater than $v_s/2$ are passed to the imaging system of the camera. Such post-filtering of the electronics is illustrated in FIG. 9c. The product of MTF conditions represented by FIGS. 9b and 9c again are represented in FIG. 9d which, particularly when compared with the corresponding FIG. 8d reveals the elimination of aliasing phenomena.

Turning now to the prefiltering or corrective funcions carried out by the collimator in controlling aliasing phenomena, it may be observed from the foregoing that the system resolution of an orthogonal strip germanium detector type gamma camera is determined by the collimator resolution, the strip width spacing, and the resolution of the spatial channel readout electronics. The collimator is assumed to have a Gaussian point spread function (PSF) and FWHM spatial resolution $R_c$. In accordance with the invention, the value of $R_c$ should be equal to or greater than about 1.7 (l), where l is the center-to-center strip spacing in one dimension of the detector. A more detailed discussion of the derivation of this value is provided in publication XIX identified hereinabove and incorporated herein by reference.

Looking now to the specific design parameters of the collimator of the invention, it may be recalled that collimator resolution, $R_c$, has been derived geometrically at equation (1) given hereinabove. By now substituting the ideal valuation, 1.7 (l) now determined for anti-aliasing prefiltering on the part of the collimator, the inventive collimator geometry or structure may be defined. Accordingly, the collimator is defined under the following expression:

$$1.7\,(l) \leq \frac{D}{A_E(A + B + C)} \quad (7)$$

The collimator further can be defined utilizinng equation (5) above for septal wall thickness once the values of the parameter of equation (7) are determined. Further, given the value, $R_c$, for collimator resolution and the geometric parameters determined thereby as described above, the collimator geometric efficiency, $\phi_s$, as given in equation (6) above, can be applied to further maximize the performance of the collimator. Additionally, it may be noted that by suppressing frequencies above $v_s/2$ input signal contributions to aliasing phenomena are accommodated for.

Since certain changes may be made in the above system and apparatus without departing from the scope of the invention herein involved, it is intended that all matter contained in the above description or shown in the accompanying drawings shall be interpreted as illustrative and not in a limiting sense.

We claim:

1. In a gamma camera type device for deriving image defining information of the source distribution of gamma rays providing a photon energy level, E, of interest, said device including an orthogonal strip array semi-conductor for deriving spatial and energy level information corresponding with said distribution, said detector array of strips having a frequency $v_s$ and strip spacing, l, said device further including collimator means operatively associated with said detector and having an inwardly disposed plane defining side spaced from the midplane of said detector a distance, C, having an outwardly disposed plane defining side spaced from said inward side to define thickness, A, and spaced from said source a distance, B; the improvement wherein said collimator means comprises:

an array of adjacently disposed channels, having internal surfaces and disposed intermediate of said inward and outward sides, said array being configured to define a septal thickness, T, intermediate said channels, an effective collimator thickness, $A_E = A - [2/\mu(E)]$, and $\mu(E)$ is the attenuation coefficient of the surface defining material of said channels, for said energy level, E, said channels having a channel cross sectional area of effective diameter, D; and said collimator means having a collimator resolution, $R_c$, equal to or greater than about 1.7 (l) and being configured in substantial satisfaction of the expression:

$$R_c = (D/A_E)(A + B + C).$$

2. The improved gamma camera device of claim 1 wherein said internal surface of said array of adjacently disposed channels are configured as channel sides defining a square internal channel cross-section.

3. The improved gamma camera device of claim 2 wherein said array of channels comprises a plurality of sheet members of height, $h$, each configured having a plurality of mutually equally spaced, parallel slots of length equal to or about, $h/2$, and of width, $w$; said members being mutually internested along said slots to define said array of adjacently disposed channels.

4. The improved gamma camera device of claim 3 wherein said sheet members have a thickness equal to said septal wall thickness, T, and said height, $h$, is substantially equal to said collimator means thickness, A.

5. The improved gamma camera device of claim 4 wherein said sheet members are formed of said side defining material, said material exhibiting a said attenuation coefficient $\mu(E)$ for a said energy level, E, of about 140 keV.

6. The improved gamma camera device of claim 4 wherein said sheet members are formed of tungsten.

7. The improved gamma camera device of claim 4 wherein said slots are configured having a width corresponding with said sheet member thickness plus a tolerance equal to or less than 0.001 inch.

8. The improved gamma camera device of claim 2 wherein, for said collimator resolution, $R_c$, said collimator means is configured having an optimal collimator geometric efficiency, $\phi_s$, where:

$$\theta_s = \left[\frac{0.282 D^2}{A_E(D + T)}\right]^2.$$

9. The improved gamma camera device of claim 2 wherein: said array of channels comprises a plurality of sheet members of height, $h$, each configured having a plurality of mutually equally spaced, parallel slots of length equal to or about $h/2$, and a width, $w$;

said members being mutually internested along said slots to define said array of adjacently disposed channels; and wherein, said collimator means surface-defining material is tungsten.

10. The improved gamma camera device of claim 2 wherein:

said septal wall thickness, T, is equal to or about:

$$-\frac{2D\ln P}{\mu(E)A + \ln P},$$

wherein, P, is the penetration fraction of said surface-defining material and has a value about equal to or less than 0.05;

said array of channels comprises a plurality of sheet members of height, $h$, each configured having a plurality of mutually equally spaced, parallel slots of length equal to or about, $h/2$, and of width, $w$;

said members being mutually internested along said slots to define said array of adjacently disposed channels; and said collimator means surface-defining material is tungsten.

11. The improved gamma camera device of claim 2 wherein:

said septal wall thickness, T, is equal to or about:

$$-\frac{2D\ln P}{\mu(E)A + \ln P},$$

wherein, P, is the penetration fraction of said surface-defining material and has a value about equal to or less than 0.05;

said array of channels comprises a plurality of sheet members of height, $h$, each configuration having a plurality of mutually equally spaced, parallel slots of length equal to or about, $h/2$, and of width, $w$;

said member being mutually internested along said slots to define said array of adjacently disposed channels;

said collimator means surface-defining material is tungsten; and wherein for said collimator resolution, $R_c$, said collimator means is configured having an optimal collimator geometric efficiency, $\phi s$, where:

$$\theta_s = \left[\frac{0.282D^2}{A_E(D + T)}\right]^2.$$

12. The improved gamma camera device of claim 2 wherein:

said septal wall thickness, T, is equal to or about:

$$-\frac{2D\ln P}{\mu(E)A + \ln P},$$

wherein, P, is the penetration fraction of said surface-defining material and has a value about equal to or less than 0.05;

said array of channels comprises a plurality of sheet members of height, $h$, each configured having a plurality of mutually equally spaced, parallel slots of length equal to or about, $h/2$, and of width, $w$;

said members being mutually internested along said slots to define said array of adjacently disposed channels;

said collimator means surface-defining material is tungsten;

wherein, for said collimator resolution, $R_c$, said collimator means is configured having an optimal collimator geometric efficiency, $\phi$, where:

$$\theta s = \left[\frac{0.282D^2}{A_E(D + T)}\right]^2; \text{ and}$$

said slots being configured having a width corresponding with said sheet member thickness plus a tolerance equal to or less than 0.001 inch.

13. The improved gamma camera device of claim 1 wherein said septal wall thickness, T, is equal to or about:

$$\frac{-2D\ln P}{\mu(E)A + \ln P}, \text{ and}$$

wherein, P, is the penetration fraction of said surface-defining material and has a value about equal to or less than 0.05.

14. The improved gamma camera device of claim 1 wherein said collimator means surface defining material is tungsten.

15. The improved gamma camera device of claim 1 wherein said adjacently disposed channels are aligned in mutually axially parallel fashion and normal to said planes of said inward and outward sides.

16. The improved gamma camera device of claim 1 wherein:

said septal wall thickness, T, is equal to or about:

$$-\frac{2D\ln P}{\mu(E)A + \ln P},$$

wherein, P, is the penetration fraction of said surface-defining material and has a value of about equal to or less than 0.05; and wherein said collimator means surface-defining material is selected from a group consisting of tungsten, tantallum and lead.

17. The improved gamma camera device of claim 1 wherein:

said septal wall thickness, T, is equal to or about:

$$-\frac{2D\ln P}{\mu(E)A + \ln P},$$

wherein, P, is the penetration fraction of said surface-defining material and has a value about equal to or less than 0.05; and wherein, for sid collimator resolution, $R_c$, said collimator means if configured having an optimal collimator geometric efficiency, $\phi s$, where:

$$\theta_s = \left[\frac{0.282D^2}{A_E(D + T)}\right]^2.$$

18. In a gamma camera of a variety operative to derive image defining information of the source distribution of gamma rays exhibiting a select energy level, E, said camera incorporating an orthogonal strip array semiconductor detector for deriving spatial and energy level information corresponding with said distribution, said detector strips having a spatial frequency, $v_s$, and center-to-center strip spacing, l, an improved collimator comprising:

a plurality of sheet members of height, $h$, each said sheet member being configured having sheet number of parallel slots extending from one edge thereof along said height a distance substantially equivalent to the value $h/2$ and mutually spaced in a regularly recurring manner to define a slot-to-slot pitch substantially equivalent to D + T and slot width of T + e, wherein $e$ is a predetermined tolerance dimension; any given two of said sheet members being mutually internested about a select said slot of each to form a parallel multiple channel collimator assembly each said channel of which exhibits a square channel cross-section of side dimension, D, and septal thickness, T.

19. The improved gamma camera 18 wherein said collimator sheet members have a thickness, T.

20. The improved gamma camera of claim 18 wherein said sheet material is formed from the group consisting of tungsten and tantalum; and said slots are formed by chemically etching.

21. The improved gamma camera of claim 18 in which said slots pitch is selected in correspondence with said detector center-to-center strip spacing, l.

* * * * *